US010537380B2

(12) United States Patent
Houser et al.

(10) Patent No.: US 10,537,380 B2
(45) Date of Patent: Jan. 21, 2020

(54) SURGICAL INSTRUMENT WITH CHARGING STATION AND WIRELESS COMMUNICATION

(71) Applicant: Ethicon Endo-Surgery, LLC, Guaynabo, PR (US)

(72) Inventors: Kevin L. Houser, Springboro, OH (US); Daniel W. Price, Loveland, OH (US); Gavin M. Monson, Oxford, OH (US); Hitesh Jain, Chittorgarh (IN)

(73) Assignee: Ethicon LLC, Guaynabo, PR (US)

( * ) Notice: Subject to any disclaimer, the term of this patent is extended or adjusted under 35 U.S.C. 154(b) by 196 days.

(21) Appl. No.: 15/229,418

(22) Filed: Aug. 5, 2016

(65) Prior Publication Data

US 2016/0338760 A1 Nov. 24, 2016

Related U.S. Application Data

(63) Continuation of application No. 13/275,547, filed on Oct. 18, 2011, now abandoned.
(Continued)

(51) Int. Cl.
*A61B 34/00* (2016.01)
*A61B 18/14* (2006.01)
(Continued)

(52) U.S. Cl.
CPC .... *A61B 18/1442* (2013.01); *A61B 17/00234* (2013.01); *A61B 17/2812* (2013.01);
(Continued)

(58) Field of Classification Search
CPC .............. A61B 34/25; A61B 2034/252; A61B 2034/254; A61B 2034/256; A61B 2034/258
(Continued)

(56) References Cited

U.S. PATENT DOCUMENTS 1,754,806 A  4/1930  Stevenson
3,297,192 A  1/1967  Swett
(Continued)

FOREIGN PATENT DOCUMENTS

CN  101819334 A  4/2013
DE  102008051866  10/2010
(Continued)

OTHER PUBLICATIONS

U.S. Appl. No. 13/151,488.
(Continued)

*Primary Examiner* — Ahmed M Farah
(74) *Attorney, Agent, or Firm* — Frost Brown Todd LLC

(57) ABSTRACT

An apparatus comprises an electrically power surgical instrument having a handle assembly. The apparatus also comprises a communication device positioned within the handle assembly. The communication device is operable to communicate with at least a portion of the electrically powered surgical instrument. The apparatus further comprises an external device in wireless communication with the communication device. The external device is operable to receive information from the communication device and the external device is operable to provide an output viewable to the user.

16 Claims, 10 Drawing Sheets

Related U.S. Application Data

(60) Provisional application No. 61/487,846, filed on May 19, 2011, provisional application No. 61/410,603, filed on Nov. 5, 2010.

(51) Int. Cl.

| | | |
|---|---|---|
| *A61B 90/40* | (2016.01) | |
| *A61B 17/00* | (2006.01) | |
| *A61B 18/00* | (2006.01) | |
| *A61B 18/04* | (2006.01) | |
| *A61B 18/12* | (2006.01) | |
| *H02J 7/00* | (2006.01) | |
| *A61B 46/10* | (2016.01) | |
| *A61B 90/00* | (2016.01) | |
| *A61B 17/28* | (2006.01) | |
| *A61N 7/00* | (2006.01) | |
| *H01M 2/10* | (2006.01) | |
| *H01M 2/26* | (2006.01) | |
| *H01M 10/46* | (2006.01) | |
| *H01M 10/48* | (2006.01) | |
| *H02J 7/02* | (2016.01) | |
| *A61B 17/064* | (2006.01) | |
| *A61B 17/285* | (2006.01) | |
| *A61B 17/29* | (2006.01) | |
| *A61B 17/32* | (2006.01) | |

(52) U.S. Cl.
CPC .......... *A61B 18/00* (2013.01); *A61B 18/04* (2013.01); *A61B 18/12* (2013.01); *A61B 18/1206* (2013.01); *A61B 18/14* (2013.01); *A61B 18/1445* (2013.01); *A61B 34/25* (2016.02); *A61B 46/10* (2016.02); *A61B 90/08* (2016.02); *A61B 90/40* (2016.02); *A61N 7/00* (2013.01); *H01M 2/10* (2013.01); *H01M 2/1016* (2013.01); *H01M 2/26* (2013.01); *H01M 10/46* (2013.01); *H01M 10/48* (2013.01); *H02J 7/0044* (2013.01); *H02J 7/0045* (2013.01); *H02J 7/0047* (2013.01); *H02J 7/025* (2013.01); *A61B 17/064* (2013.01); *A61B 17/285* (2013.01); *A61B 18/1233* (2013.01); *A61B 2017/0046* (2013.01); *A61B 2017/00084* (2013.01); *A61B 2017/0084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2017/320069* (2017.08); *A61B 2017/320071* (2017.08); *A61B 2017/320094* (2017.08); *A61B 2017/320095* (2017.08); *A61B 2018/0019* (2013.01); *A61B 2018/00178* (2013.01); *A61B 2018/00589* (2013.01); *A61B 2018/00595* (2013.01); *A61B 2018/00601* (2013.01); *A61B 2018/00607* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *H01M 2220/30* (2013.01); *H02J 2007/005* (2013.01); *Y10T 29/49005* (2015.01); *Y10T 29/49895* (2015.01); *Y10T 29/53913* (2015.01)

(58) Field of Classification Search
USPC ...................... 606/1, 130; 128/898
See application file for complete search history.

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,641,077 A | 2/1987 | Pascaloff |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,357,732 A | 10/1994 | Markle et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,452,391 A | 9/1995 | Chou et al. |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,371 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,893,835 A | 4/1999 | Witt et al. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | DiMatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |

(56) References Cited

U.S. PATENT DOCUMENTS

| | | |
|---|---|---|
| 6,099,537 A | 8/2000 | Sugai et al. |
| 6,113,593 A | 9/2000 | Tu et al. |
| 6,113,596 A | 9/2000 | Hooven et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,517,561 B1 | 2/2003 | Phillips |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 * | 3/2004 | Francischelli ......... A61B 5/411 128/898 |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,160,132 B2 | 1/2007 | Phillips et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger et al. |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,353,068 B2 | 4/2008 | Tanaka et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,375,644 B2 | 5/2008 | Miyazawa |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,470,237 B2 | 12/2008 | Beckman et al. |
| 7,473,145 B2 | 1/2009 | Her et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,570,994 B2 | 8/2009 | Tamura et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,699,850 B2 | 4/2010 | Miller |
| 7,699,856 B2 | 4/2010 | Van Wyk et al. |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,923,151 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,083,120 B2 | 12/2011 | Shelton et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,179,103 B2 | 5/2012 | Doljack |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,323,271 B2 | 12/2012 | Humayun et al. |
| 8,328,732 B2 | 12/2012 | Parihar et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |

(56) References Cited

U.S. PATENT DOCUMENTS

| | | |
|---|---|---|
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,459,520 B2 | 6/2013 | Giordano et al. |
| 8,461,744 B2 | 6/2013 | Wiener et al. |
| 8,487,487 B2 | 7/2013 | Dietz et al. |
| 8,522,795 B2 | 9/2013 | Bouix et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,574,253 B2 | 11/2013 | Gruber et al. |
| 8,598,852 B2 | 12/2013 | Gilmore |
| 8,602,287 B2 | 12/2013 | Laurent et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,636,736 B2 | 1/2014 | Yates et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanta et al. |
| 8,968,648 B2 | 3/2015 | Kaneko |
| 8,986,302 B2 | 3/2015 | Boudreaux et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,125 B2 | 6/2015 | Boudreaux |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,095,346 B2 | 8/2015 | Houser et al. |
| 9,113,903 B2 | 8/2015 | Unger et al. |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,408,575 B2 | 8/2016 | Bordoley et al. |
| 9,421,062 B2 | 8/2016 | Houser et al. |
| 9,820,738 B2* | 11/2017 | Lytle, IV ............... A61B 90/98 |
| 10,004,497 B2* | 6/2018 | Overmyer ............. A61B 90/98 |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0078484 A1 | 4/2007 | Talarico et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1* | 7/2008 | Cao ........................ A61B 18/22 606/10 |
| 2008/0164842 A1 | 7/2008 | Bergner |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, III et al. |
| 2008/0255413 A1 | 10/2008 | Zemlok et al. |
| 2008/0281254 A1* | 11/2008 | Humayun ............. A61B 90/98 604/22 |
| 2008/0281301 A1 | 11/2008 | Deboer et al. |
| 2008/0315829 A1 | 12/2008 | Jones et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0143799 A1 | 6/2009 | Smith et al. |
| 2009/0143800 A1 | 6/2009 | Deville et al. |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0076455 A1 | 3/2010 | Birkenbach et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0121049 A1* | 5/2011 | Malinouskas .... A61B 17/07207 227/175.1 |
| 2011/0221398 A1 | 9/2011 | Ferber |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |

(56) References Cited

U.S. PATENT DOCUMENTS

| | | | |
|---|---|---|---|
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116267 A1 | 5/2012 | Kimball et al. |
| 2012/0116366 A1 | 5/2012 | Houser et al. |
| 2012/0116380 A1 | 5/2012 | Madan |
| 2012/0116381 A1 | 5/2012 | Houser et al. |
| 2012/0116388 A1 | 5/2012 | Houser et al. |
| 2012/0116391 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090552 A1 | 4/2013 | Ramamurthy et al. |
| 2013/0090675 A1 | 4/2013 | Mumaw et al. |
| 2013/0118733 A1 | 5/2013 | Kumar |
| 2014/0088739 A1 | 3/2014 | Ellis et al. |
| 2015/0305763 A1 | 10/2015 | Houser et al. |
| 2016/0121143 A1 | 5/2016 | Mumaw et al. |
| 2016/0206900 A1 | 7/2016 | Haberstich et al. |
| 2016/0329614 A1 | 11/2016 | Madan et al. |

FOREIGN PATENT DOCUMENTS

| | | |
|---|---|---|
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 2425874 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 2440566 A | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| JP | H 01-268370 | 10/1989 |
| JP | H 10-308907 | 11/1998 |
| JP | 2002-336265 | 11/2002 |
| JP | 2005-033868 | 2/2005 |
| JP | 2010-518978 | 6/2010 |
| JP | 5410110 B | 2/2014 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/050439 | 5/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,503.
U.S. Appl. No. 13/269,870.
U.S. Appl. No. 13/270,701.
U.S. Appl. No. 13/274,480.
U.S. Appl. No. 13/274,496.
U.S. Appl. No. 13/274,507.
U.S. Appl. No. 13/275,495.
U.S. Appl. No. 13/275,547.
U.S. Appl. No. 13/275,563.
U.S. Appl. No. 13/276,673.
U.S. Appl. No. 13/276,707.
U.S. Appl. No. 13/277,328.
U.S. Appl. No. 14/788,915.
U.S. Appl. No. 14/992,104.
U.S. Appl. No. 15/008,350.
U.S. Appl. No. 15/212,423.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
Australian First Examination Report dated May 18, 2015 for Application No. AU2011323284.
Chinese Office Action dated Jan. 29, 2015 for Application No. 2011800638159.
Chinese Office Action dated Jan. 29, 2015 for Application No. 2011800640106.
Chinese Office Action dated Feb. 2, 2015 for Application No. 2011800534501.
Chinese Office Action dated Feb. 2, 2015 for Application No. 2011800641490.
Chinese Office Action dated Feb. 6, 2015 for Application No. 2011800638356.
Chinese Office Action dated Feb. 16, 2015 for Application No. 2011800638286.
Chinese Office Action dated Feb. 28, 2015 for Application No. 2011800641471.
Chinese Office Action dated Mar. 4, 2015 for Application No. 201180063595.X.
Chinese Office Action dated Mar. 27, 2015 for Application No. 2011800638214.
Chinese Office Action dated Mar. 30, 2015 for Application No. 2011800639823.
Chinese Office Action dated Apr. 16, 2015 for Application No. 201180063919X.
Chinese Office Action dated Apr. 20, 2015 for Application No. 2011800534342.
Chinese Office Action dated Aug. 28, 2015 for Application No. 2011800640106.
EP Communication dated Feb. 19, 2014 for Application. No. EP 11781972.2.
International Search Report and Written Opinion dated Jan. 26, 2012 for Application No. PCT/US2011/059212.
International Preliminary Report on Patentability dated May 7, 2013 for Application No. PCT/US2011/059212.
Communication from International Searching Authority dated Jan. 24, 2012 for Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.

(56) References Cited

OTHER PUBLICATIONS

International Search Report dated Feb. 13, 2012 for Application No. PCT/US2011/059217.
International Preliminary Report on Patentability dated May 7, 2013 for Application No. PCT/US2011/059217.
International Search Report dated Jun. 12, 2012 for Application No. PCT/US2011/059218.
International Preliminary Report on Patentability dated May 7, 2013 for Application No. PCT/US2011/059218.
International Search Report dated Jan. 26, 2012 for Application No. PCT/US11/059220.
International Preliminary Report on Patentability dated May 7, 2013 for Application No. PCT/US2011/059220.
Communication from International Searching Authority dated Feb. 2, 2012 for Application No. PCT/US2011/059222.
International Search Report dated Apr. 18, 2012 for Application No. PCT/US2011/059222.
International Preliminary Report on Patentability dated May 7, 2013 for Application No. PCT/US2011/059222.
International Search Report dated Feb. 1, 2012 for Application No. PCT/US11/059223.
International Preliminary Report on Patentability dated Feb. 1, 2012 for Application No. PCT/US2011/059223.
International Search Report dated Jan. 12, 2012 for Application No. PCT/US11/059226.
International Preliminary Report on Patentability dated May 7, 2013 for Application No. PCT/US2011/059226.
International Search Report dated Mar. 15, 2012 for Application No. PCT/US2011/059338.
International Preliminary Report on Patentability dated May 7, 2013 for Application No. PCT/US2011/059338.
International Search Report dated Feb. 7, 2012 for Application No. PCT/US2011/059351.
International Preliminary Report on Patentability dated May 7, 2013 for Application No. PCT/US2011/059351.
International Search Report dated Feb. 2, 2012 for Application No. PCT/US2011/059354.
International Preliminary Report on Patentability dated May 7, 2013 for Application No. PCT/US2011/059354.
International Search Report dated May 29, 2012 for Application No. PCT/US11/059358.
International Preliminary Report on Patentability dated May 7, 2013 for Application No. PCT/US2011/059358.
Communication from International Searching Authority dated Feb. 6, 2012 for Application No. PCT/US2011/059362.
International Search Report dated Mar. 22, 2012 for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from International Searching Authority dated Feb. 2, 2012 for Application No. PCT/US2011/059378.
International Search Report dated May 24, 2012 for Application No. PCT/US2011/059378.
International Search Report and Written Opinion dated Feb. 2, 2012 for Application No. PCT/US2011/059378.
International Preliminary Report on Patentability dated May 7, 2013 for Application No. PCT/US2011/059378.
International Search Report dated Apr. 11, 2012 for Application No. PCT/US2011/059381.
International Search Report and Written Opinion dated Jul. 6, 2012 for PCT/US2011/059381.
International Preliminary Report on Patentability dated May 8, 2013 for Application No. PCT/US2011/059381.
Japanese Office Action, Notification of Reasons for Refusal, dated Sep. 1, 2015 for Application No. 2013-537837.
Japanese Office Action, Notification of Reasons for Refusal, dated Sep. 1, 2015 for Application No. 2013-537866.
Japanese Office Action, Notification of Reasons for Refusal, dated Oct. 6, 2015 for Application No. 2013-537869.
Office Action Non-Final dated Aug. 6, 2013 for U.S. Appl. No. 13/151,471.
Notice of Allowance dated Dec. 6, 2013 for U.S. Appl. No. 13/151,471.
Office Action Non Final dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
U.S. Office Action, Non-Final, dated Aug. 14, 2014 for U.S. Appl. No. 13/151,481.
U.S. Office Action, Final, dated Apr. 1, 2015 for U.S. Appl. No. 13/151,481.
U.S. Office Action, Notice of Allowance, dated Jun. 10, 2015 for U.S. Appl. No. 13/151,481.
Restriction Requirement dated Jul. 5, 2013 for U.S. Appl. No. 13/151,488.
U.S. Office Action, Non-Final, dated Nov. 7, 2014 for U.S. Appl. No. 13/151,488.
U.S. Office Action, Final, dated Jul. 17, 2015 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Office Action Non Final dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for Application No. 13/151,498.
U.S. Office Action, Non-Final, dated Jun. 8, 2014 for U.S. Appl. No. 13/151,503.
U.S. Office Action, Non-Final, dated Nov. 6, 2014 for U.S. Appl. No. 13/151,503.
U.S. Office Action, Final, dated Jun. 8, 2015 for U.S. Appl. No. 13/151,503.
U.S. Office Action, Non-Final, dated Oct. 2, 2015 for U.S. Appl. No. 13/151,503.
Restriction Requirement dated Mar. 13, 2013 for U.S. Appl. No. 13/151,509.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Jan. 29, 2014 for U.S. Appl. No. 13/151,509.
Office Action Non-Final dated Jul. 9, 2014 for U.S. Appl. No. 13/151,509.
U.S. Office Action, Notice of Allowance, dated Oct. 28, 2014 for U.S. Appl. No. 13/151,509.
U.S. Office Action, Notice of Allowance, dated Feb. 25, 2015 for U.S. Appl. No. 13/151,509.
Restriction Requirement dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Notice of Allowance, dated Feb. 17, 2015 for U.S. Appl. No. 13/151,512.

(56) References Cited

OTHER PUBLICATIONS

U.S. Office Action, Restriction Requirement, dated Jul. 11, 2014 for U.S. Appl. No. 13/269,870.
U.S. Office Action, Non-Final, dated Jan. 5, 2015 for U.S. Appl. No. 13/269,870.
Restriction Requirement dated Feb. 28, 2013 for U.S. Appl. No. 13/270,667.
Office Action Non-Final dated Apr. 26, 2013 for U.S. Appl. No. 13/270,667.
Office Action Final dated Oct. 25, 2013 for U.S. Appl. No. 13/270,667.
U.S. Office Action, Non-Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Final, dated Mar. 17, 2015 for U.S. Appl. No. 13/270,684.
U.S. Office Action, Notice of Allowance, dated Jul. 28, 2015 for U.S. Appl. No. 13/270,684.
U.S. Office Action, Restriction Requirement, dated Sep. 11, 2014 for U.S. Appl. No. 13/270,701.
U.S. Office Action, Non-Final, dated Dec. 16, 2014 for U.S. Appl. No. 13/270,701.
U.S. Office Action, Final, dated Jun. 17, 2015 for U.S. Appl. No. 13/270,701.
Office Action Non-Final dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Non-Final, dated Mar. 26, 2015 for U.S. Appl. No. 13/271,352.
U.S. Office Action, Final, dated Jul. 15, 2015 for U.S. Appl. No. 13/271,352.
U.S. Office Action, Restriction Requirement, dated Feb. 25, 2015 for U.S. Appl. No. 13/271,364.
U.S. Office Action, Non-Final, dated Jul. 14, 2015 for U.S. Appl. No. 13/271,364.
U.S. Office Action, Restriction Requirement, dated Oct. 2, 2013 for U.S. Appl. No. 13/274,480.
Office Action Non-Final dated Feb. 14, 2014 for U.S. Appl. No. 13/274,480.
U.S. Office Action, Final, dated Jul. 17, 2014 for U.S. Appl. No. 13/274,480.
U.S. Office Action, Non-Final, dated May 1, 2015 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
U.S. Office Action, Final, dated Aug. 22, 2014 for U.S. Appl. No. 13/274,496.
U.S. Office Action, Non-Final, dated Apr. 2, 2015 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
U.S. Office Action, Non-Final, dated Jul. 22, 2015 for U.S. Appl. No. 13/274,507.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 6, 2013 for U.S. Appl. No. 13/274,516.
Office Action Final dated Jun. 12, 2014 for U.S. Appl. No. 13/274,516.
U.S. Office Action, Non-Final, dated Oct. 8, 2014 for U.S. Appl. No. 13/274,516.
U.S. Office Action, Final, dated May 8, 2015 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Final dated Oct. 25, 2013 for U.S. Appl. No. 13/274,540.
U.S. Office Action, Non-Final, dated Aug. 26, 2014 for U.S. Appl. No. 13/274,540.
U.S. Office Action, Notice of Allowance, dated Jan. 21, 2015 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
U.S. Office Action, Non-Final, dated Aug. 14, 2014 for U.S. Appl. No. 13/274,805.
U.S. Office Action, Notice of Allowance, dated Nov. 28, 2014 for U.S. Appl. No. 13/274,805.
U.S. Office Action, Notice of Allowance, dated Jan. 21, 2015 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Office Action Final dated Nov. 26, 2013 for U.S. Appl. No. 13/274,830.
U.S. Office Action, Non-Final, dated Oct. 22, 2014 for U.S. Appl. No. 13/274,830.
U.S. Office Action, Notice of Allowance, dated Mar. 23, 2015 for U.S. Appl. No. 13/274,830.
U.S. Office Action, Notice of Allowance, dated Jul. 9, 2015 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Final dated Dec. 5, 2013 for U.S. Appl. No. 13/275,495.
U.S. Office Action, Non-Final, dated Feb. 25, 2015 for U.S. Appl. No. 13/275,495.
U.S. Office Action, Final, dated May 27, 2015 for U.S. Appl. No. 13/275,495.
Office Action Non-Final dated Jan. 6, 2014 for U.S. Appl. No. 13/275,514.
U.S. Office Action, Non-Final, dated Sep. 9, 2014 for U.S. Appl. No. 13/275,514.
U.S. Office Action, Non-Final, dated May 21, 2015 for U.S. Appl. No. 13/275,514.
U.S. Office Action, Final, dated Sep. 11, 2015 for U.S. Appl. No. 13/275,514.
U.S. Office Action, Notice of Allowance, dated Nov. 25, 2015 for U.S. Appl. No. 13/275,514.
Office Action Non-Final dated May 17, 2013 for U.S. Appl. No. 13/275,547.
Office Action Final dated Feb. 28, 2014 for U.S. Appl. No. 13/275,547.
U.S. Office Action, Non-Final, dated Aug. 20, 2014 for U.S. Appl. No. 13/275,547.
U.S. Office Action, Final, dated Mar. 10, 2015 for U.S. Appl. No. 13/275,547.
U.S. Office Action, Non-Final, dated Aug. 28, 2015 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
U.S. Office Action, Non-Final, dated Oct. 23, 2014 for U.S. Appl. No. 13/275,563.
U.S. Office Action, Non-Final, dated May 28, 2015 for U.S. Appl. No. 13/275,563.
Restriction Requirement dated Feb. 6, 2013 for U.S. Appl. No. 13/276,660.

(56) References Cited

OTHER PUBLICATIONS

Office Action Non-Final dated Jun. 3, 2013 for U.S. Appl. No. 13/246,660.
U.S. Office Action, Restriction Requirement, dated Jul. 9, 2014 for U.S. Appl. No. 13/276,660.
U.S. Office Action, Notice of Allowance, dated Jun. 17, 2015 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Office Action Final dated Mar. 21, 2014 for U.S. Appl. No. 13/276,673.
U.S. Office Action, Non-Final, dated Aug. 14, 2014 for U.S. Appl. No. 13/276,673.
U.S. Office Action, Final, dated Mar. 13, 2015 for U.S. Appl. No. 13/276,673.
Restriction Requirement dated Feb. 6, 2013 for U.S. Appl. No. 13/276,687.
Office Action Non Final dated Jun. 12, 2013 for U.S. Appl. No. 13/276,687.
Notice of Allowance dated Nov. 12, 2013 for U.S. Appl. No. 13/276,687.
Notice of Allowance dated Jun. 2, 2014 for U.S. Appl. No. 13/276,687.
U.S. Office Action, Notice of Allowance, dated Sep. 12, 2014 for U.S. Appl. No. 13/276,687.
U.S. Office Action, Notice of Allowance, dated Dec. 23, 2014 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Office Action Final dated Sep. 27, 2013 for U.S. Appl. No. 13/276,707.
U.S. Office Action, Non-Final, dated Jan. 29, 2015 for U.S. Appl. No. 13/276,707.
U.S. Office Action, Non-Final, dated Jul. 16, 2015 for U.S. Appl. No. 13/276,707.
Restriction Requirement dated Feb. 6, 2013 for U.S. Appl. No. 13/276,725.
U.S. Office Action, Non-Final, dated Aug. 20, 2014 for U.S. Appl. No. 13/276,725.
U.S. Office Action, Notice of Allowance, dated Mar. 13, 2015 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Final dated Nov. 08, 013 for U.S. Appl. No. 13/276,745.
Office Action Non-Final dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Restriction Requirement, dated Sep. 24, 2014 for U.S. Appl. No. 13/277,328.
U.S. Office Action, Non-Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
Japanese Office Action, Notification of Reasons for Refusal, dated Feb. 16, 2016 for Application No. 2013-537837.
Japanese Office Action, Notification of Reasons for Refusal, dated Jun. 28, 2016 for Application No. 2013-537866.
U.S. Office Action, Final, dated Mar. 9, 2016 for U.S. Appl. No. 13/151,503.
U.S. Office Action, Notice of Allowance, dated Jul. 27, 2016 for U.S. Appl. No. 13/151,503.
U.S. Office Action, Non-Final, dated Jun. 6, 2016 for U.S. Appl. No. 13/275,495.
U.S. Office Action, Notice of Allowance, dated Mar. 2, 2016 for U.S. Appl. No. 13/275,514.
U.S. Office Action, Final, dated May 6, 2016 for U.S. Appl. No. 13/275,547.
Chinese Search Report dated Oct. 8, 2016 for App. No. CN 2011800534342.
Chinese Third Office Action dated Oct. 17, 2016 for App. No. CN 2011800534342.
Japanese Office Action, Pretrial Examination Report, dated Aug. 2, 2016 for Application No. 2013-537837.
Japanese Office Action, Examiner's Decision of Refusal, dated Sep. 13, 2016 for Application No. 2013-537869.
U.S. Office Action, Notice of Allowance, dated Nov. 2, 2016 for U.S. Appl. No. 13/151,503.
U.S. Office Action, Final, dated Dec. 21, 2016 for U.S. Appl. No. 13/275,495.
Indian Office Action, Examination Report, dated Mar. 28, 2018 for Application No. 4008/DELNP/2013, 6 pgs.
Indian Office Action, Examination Report, dated Jun. 13, 2019 for Application No. 3973/DELNP/2013, 6 pgs.

* cited by examiner

SURGICAL INSTRUMENT WITH CHARGING STATION AND WIRELESS COMMUNICATION

PRIORITY

This application is a continuation of U.S. patent application Ser. No. 13/275,547, entitled "Surgical Instrument with Charging Station and Wireless Communication," filed on Oct. 18, 2011, published as U.S. Patent Pub. No. 2012/0116381 on May 10, 2012, now abandoned, which claims priority to U.S. Provisional Application Ser. No. 61/410,603, filed Nov. 5, 2010, entitled "Energy-Based Surgical Instruments," the disclosure of which is incorporated by reference herein. U.S. patent application Ser. No. 13/275,547, now abandoned, also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical instruments since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
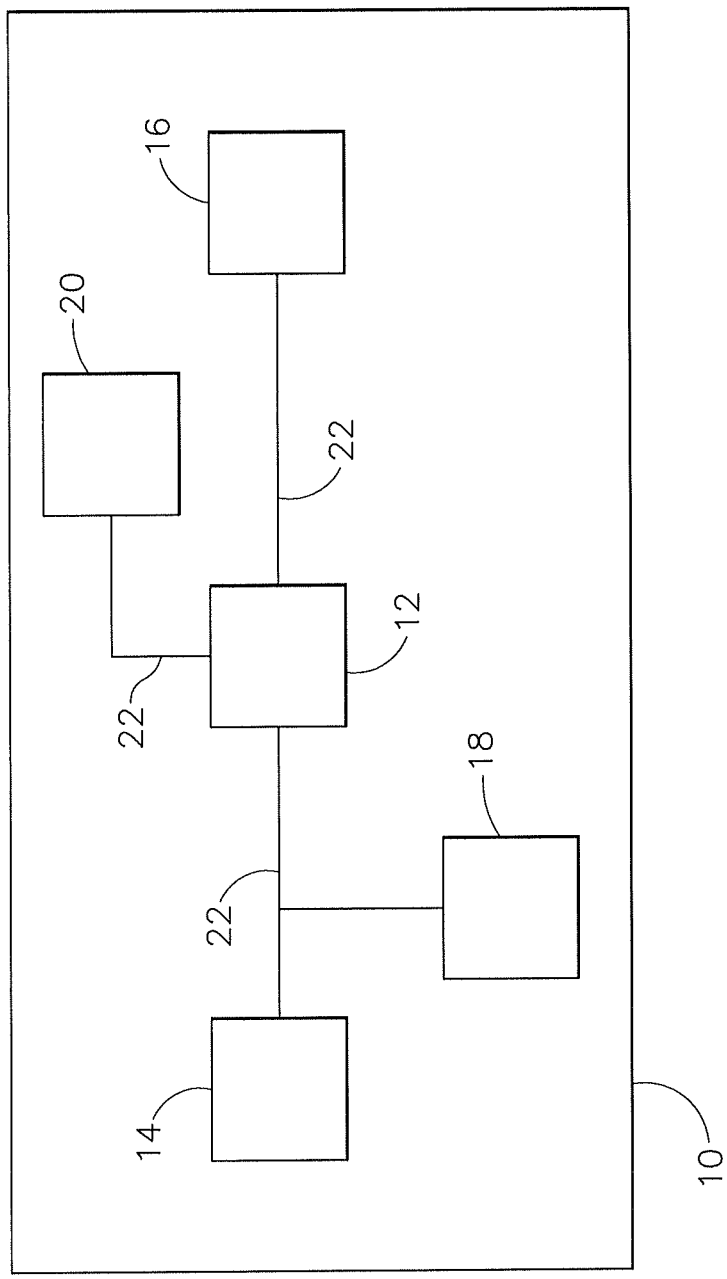
FIG. 1 depicts a schematic view of an exemplary medical device having an internal power source.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

I. Medical Devices for Use with Insertable or Reclaimable Components

FIG. 1 shows components of an exemplary medical device and/or surgical instrument (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
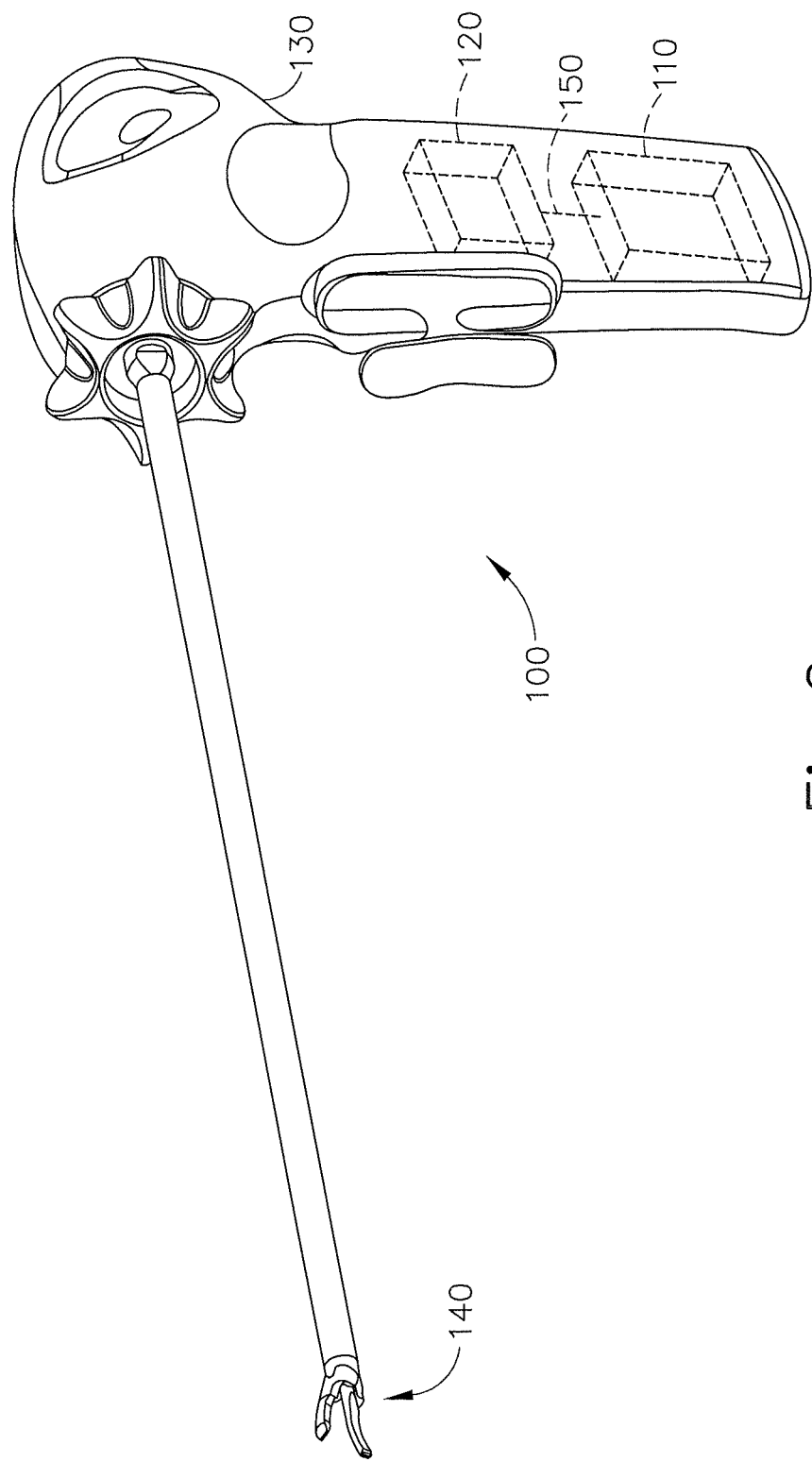
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. As is readily apparent, this may allow the power source (110) to be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein. While certain configurations of an exemplary medical device (100) have been described, various other ways in which medical device (100) may be configured will be apparent to those of ordinary skill in the art in view of the teachings herein.

By way of example only, medical devices (10, 100) and/or any other medical device referred to herein may be constructed in accordance with at least some of the teachings of U.S. Pat. Nos. 5,980,510; 6,500,176; 6,783,524; 7,112,201; 7,125,409; 7,169,146; 7,186,253; 7,189,233; 7,220,951; 7,309,849; 7,311,709; 7,354,440; 7,381,209; 7,416,101; 7,738,971; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0143797, issued as U.S. Pat. No. 8,419,757 on Apr. 16, 2013; U.S. Pub. No. 2009/0209990, issued as U.S. Pat. No. 8,657,174 on Feb. 25, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2011/0087218, issued as U.S. Pat. No. 8,939,974 on Jan. 27, 2015; U.S. patent application Ser. No. 13/151,481, issued as U.S. Pat. No. 9,161,803 on Oct. 20, 2015; and/or U.S. Provisional Application Ser. No. 61/410,603. The disclosures of each of those documents are incorporated by reference herein in their entirety.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary RF Communication Device

In some instances, it may be desirable to provide wireless communication of information to and/or from a medical device (10, 100). For instance, such information may relate to characteristics of medical device (10, 100), operation of medical device (10, 100), the surgical environment of medical device (10, 100) and/or other information. Such information may be stored and/or may be presented to the user of medical device (10, 100), such that the user may receive feedback in real time. Various examples of ways in which such wireless communication may be provided and implemented will be discussed in greater detail below, while additional examples will be apparent to those of ordinary skill in the art in view of the teachings herein. It should be understood that the below teachings may be readily incorporated with medical device (10, 100) and with the instruments taught in the various references cited herein.

Figure 3:
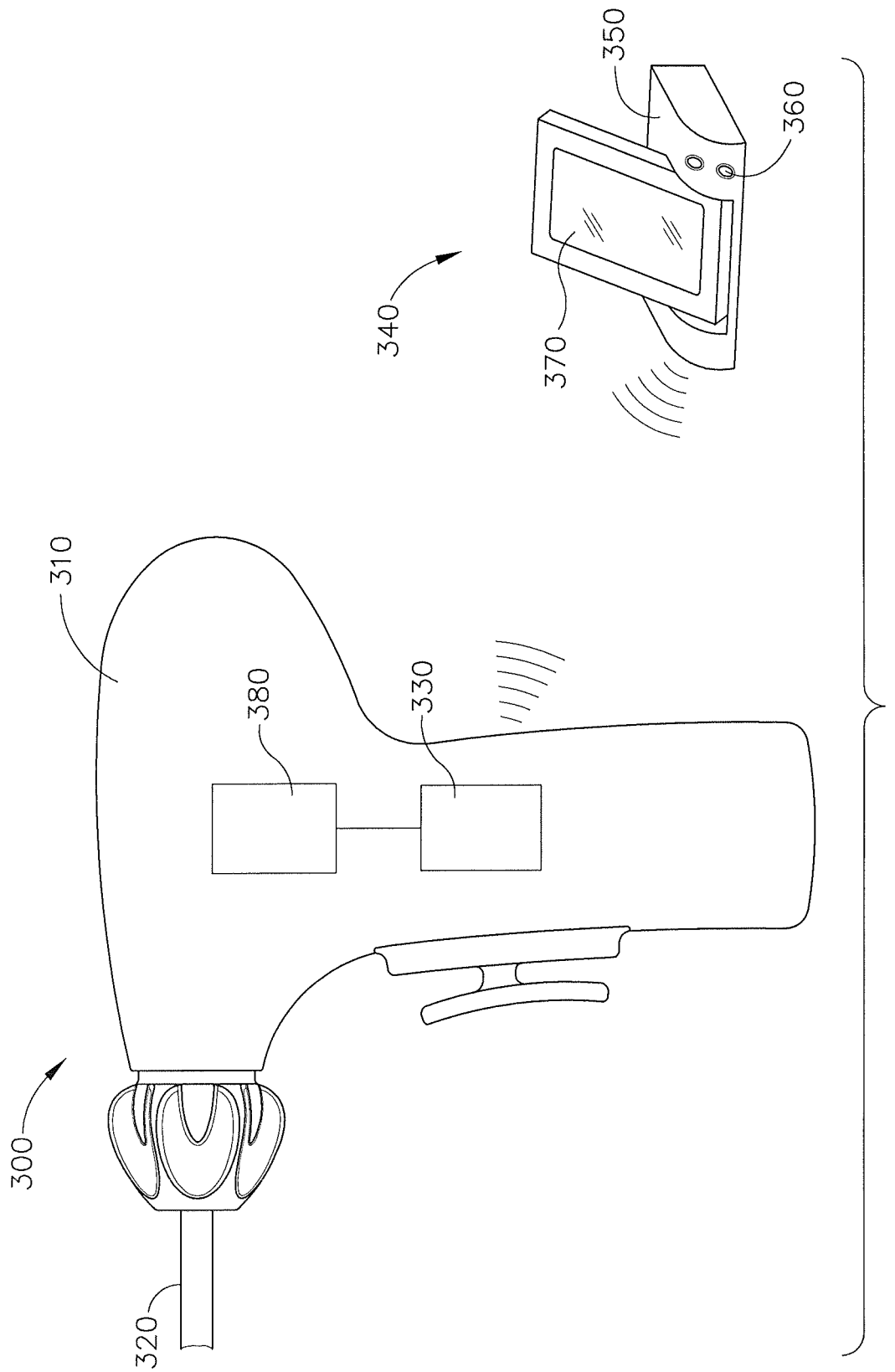
FIG. 3 depicts a diagrammatic view of an exemplary surgical instrument with an external device.

FIG. 3 depicts an exemplary surgical instrument (300) having a handle assembly (310) connected to a transmission assembly (320). Surgical instrument (300) further comprises a communication device (330) positioned in the present example within handle assembly (310). Surgical instrument (300) is further in communication with an external device (340) through communication device (330). In the exemplary versions, surgical instrument (300) is in communication with external device (340) through RF communication, but any suitable communication means may be used as would be apparent to one of ordinary skill in the art in view of the teachings herein. For example, Bluetooth communication, Wi-Fi, or any other suitable communication may be used. It will also be appreciated that a software handshake may be used to verify that surgical instrument (300) and external device (340) are authorized to communicate with each other and/or to register surgical instrument (300) with external device (340). In some other exemplary versions, surgical instrument (300) and external device (340) are operable to establish communication with each other based primarily on proximity such that surgical instrument (300) simply attempts to connect to nearby devices, such as external device (340). For instance, communication device (330) may periodically and/or continuously broadcast a signal until external device (340) responds. Conversely, external device (340) may broadcast until a communication device (330) responds.

Communication device (330) of surgical instrument (300) is in communication with a control unit (380), which may comprise a microprocessor or any other suitable computing chip as would be apparent to one of ordinary skill in the art in view of the teachings herein. It will be appreciated that control unit (380) is in communication with many or all of the working components of surgical instrument (900) through the use of sensors operable to measure parameters associated with the functionality/operation of surgical instrument (900). As a result, control unit (380) is operable to monitor the operation of surgical instrument (900) and record various diagnostic readings of surgical instrument (900). The diagnostic readings may be communicated to communication device (330); and/or, in some versions, as will be discussed in further detail below, to a memory card for storage. In addition to diagnostic information, it will be appreciated that identification information of surgical instrument (300) may be recorded. Furthermore, information regarding operation of surgical instrument (300) may be recorded as well. For example, after a use of surgical instrument (300), control unit (380) may be operable to determine whether the operation was successful or not. Other suitable pieces of information will be apparent to one of ordinary skill in the art in view of the teachings herein.

External device (340) comprises a console (350) having user controls (360), and video output (370). Video output (370) may comprise an LCD screen, an LED LCD screen, and/or a touch screen, or any other suitable screen operable to display information to the user as would be apparent to one of ordinary skill in the art in view of the teachings herein. User controls (360) comprise tactile buttons alongside video output (370), but in some other exemplary versions, user controls (360) may comprise soft keys embedded into video output (370). In some versions, user controls (360) are incorporated into video output (370) in the form of a touch screen. Other suitable components and configurations for user controls (360) will be apparent to one of ordinary skill in the art in view of the teachings herein. User controls (360) are operable to change the display of video output (370) so as to display different information to video output (370). Furthermore, user controls (360) may be operable to simply change the format of video output (370) to display the information in, for example, a different type face or different colors. In some merely exemplary versions, external device (340) may comprise software incorporated into a Smartphone, such as the iPhone or any other suitable mobile devices.

In some versions, communication device (330) is in one-way communication with external device (340) such that information is transferred only from communication device (330) of surgical instrument (300) to external device (340). For example, in the event that any errors occur during the use of surgical instrument (300), an error code may be sent wirelessly from surgical instrument (300) to external device (340). Furthermore, any other relevant diagnostic information may be sent from surgical instrument (300) to external device (340) as would be apparent to one of ordinary skill in the art in view of the teachings herein. Once an error code is sent to external device (340), external device (340) may output the error code to video output (370) for user to read the error code. In some versions, a corresponding explanation for the error code may also be output. Furthermore, console (350) may be operable to output an audible warning. The audible warning could comprise a generic warning for any error that occurs, or in other exemplary versions, audible warning may comprise a specific sound corresponding to a particular warning such that the user may be able to tell what error (if any) has occurred by simply listening to the warning. Video output (370) may further be operable to output a full diagnostic report regarding the various components of surgical instrument (300) such that a user may be able to tell version, functionality, identification, etc. information of the various components of surgical instrument (300). In yet some other exemplary versions, when an error code is transmitted to external device (350), external device (350) may be operable to send the error code information to the manufacturer or any other suitable location for reporting or diagnosis purposes. External device (350) may be operable to send the error code information by using, for example, cellular, WiFi, modem communication, or any other suitable communication means as would be apparent to one of ordinary skill in the art in view of the teachings herein. Furthermore, in addition to the error code, external device (350) may be operable to send contextual troubleshooting instructions based on the error code sent by external device (350), to enable the user to correct the errors.

If the identification of surgical instrument (300) is transmitted to external device (340), it will further be appreciated that a user manual corresponding to the model of surgical instrument (300) may be output to video output (370) and navigated using user controls (360). Furthermore, external device (340) may be operable to display useful information to a user with respect to individual components (rather than an entire user manual).

It should be understood that communication device (330) may comprise an RF communications module operable to engage in two-way communication with external device (340) such that communication device (330) may send information and/or commands to external device (340) and external device (340) may send information and/or commands to communication device (330). It will be appreciated that in a two-way communication setup, all of the features of a one-way communication may be implemented. In addition, diagnostic instructions may be sent to surgical instrument (300) via communication device (330), which may include instructions to record readings at particular sensors within surgical instrument (300) or any other suitable instructions as would be apparent to one of ordinary skill in the art in view of the teachings herein. In yet other exemplary versions, the user may be able to select a user profile on external device (340), which may then be sent to surgical instrument (300) to customize the functionality of surgical instrument (300). For example, the user may establish custom maximum and minimum settings for buttons on surgical instrument (300). In some versions, the user may use external device (340) to indicate the type of procedure to be performed using surgical instrument (300). External device (340) may use this information to selectively enable/disable certain functionalities, parameters, and/or diagnostics in surgical instrument (300). For example, the maximum power level of surgical instrument (300), the blade amplitude at various power levels of surgical instrument (300), and/or the pattern of power provided to surgical instrument (300) may be determined based on the procedure selected by the user.

In some versions, software/firmware revisions for surgical instrument (300) may be sent to surgical instrument (300), which are operable to modify various functionalities of surgical instrument (300). For example, when external device (340) is in communication with surgical instrument (300) through communication device (330), surgical instrument (300) may send firmware/software version information to external device (340). External device (340), which may be in communication with a computer or a remote site via the Internet, may then check whether the firmware version of surgical instrument (300) is the most updated version. If a newer firmware/software version exists, then external device (340) may automatically send the updated software to surgical instrument (300). In the alternative, external device (340) may send instructions prompting a user to confirm intent to receive a software update prior to sending updated software to surgical instrument (300). It will be appreciated that such software may be delivered to control unit (380) for implementation or to any other suitable component. Some other merely exemplary versions may include instructions transmitted to control unit (380) from external device (340) operable to enable and disable functionalities of surgical instrument (300). For example, the instructions may be operable to only allow surgical instrument (300) to be used a certain number of times. Furthermore, the instructions may prevent surgical instrument (300) from being used outside of particular hours. Other suitable variations of enabling and disabling components will be apparent to one of ordinary skill in the art in view of the teachings herein. In some versions, external device (340) may be operable to send automated diagnostic and/or troubleshooting commands to surgical instrument (300). For example, the user may press a key on external device (340) operable to send directions to surgical instrument (300) where the user may walk through a set of pre-defined instructions and/or routines to enable the user to diagnose and/or troubleshoot any issues with surgical instrument (300).

While the present example contemplates RF communication between communication device (330) and external device (340), it will be appreciated that any suitable method of communication between communication device (330) and external device (340) may be used. Furthermore, it is contemplated that communication device (330) and external device (340) may be located remotely in relation to each other with communication device (330) and external device (340) being in cellular communication or some other form of substantially remote communication. In versions where communication device (330) and external device (340) are in cellular communication, an intermediate cellular tower and/or other communication points may be used to transmit information between communication device (330) and external device (340). In yet other merely exemplary versions, it will be appreciated that communication device (330) and external device (340) may be in communication through a hardware connection such as a USB or Ethernet cable.

III. Exemplary Memory Unit

Figure 4:
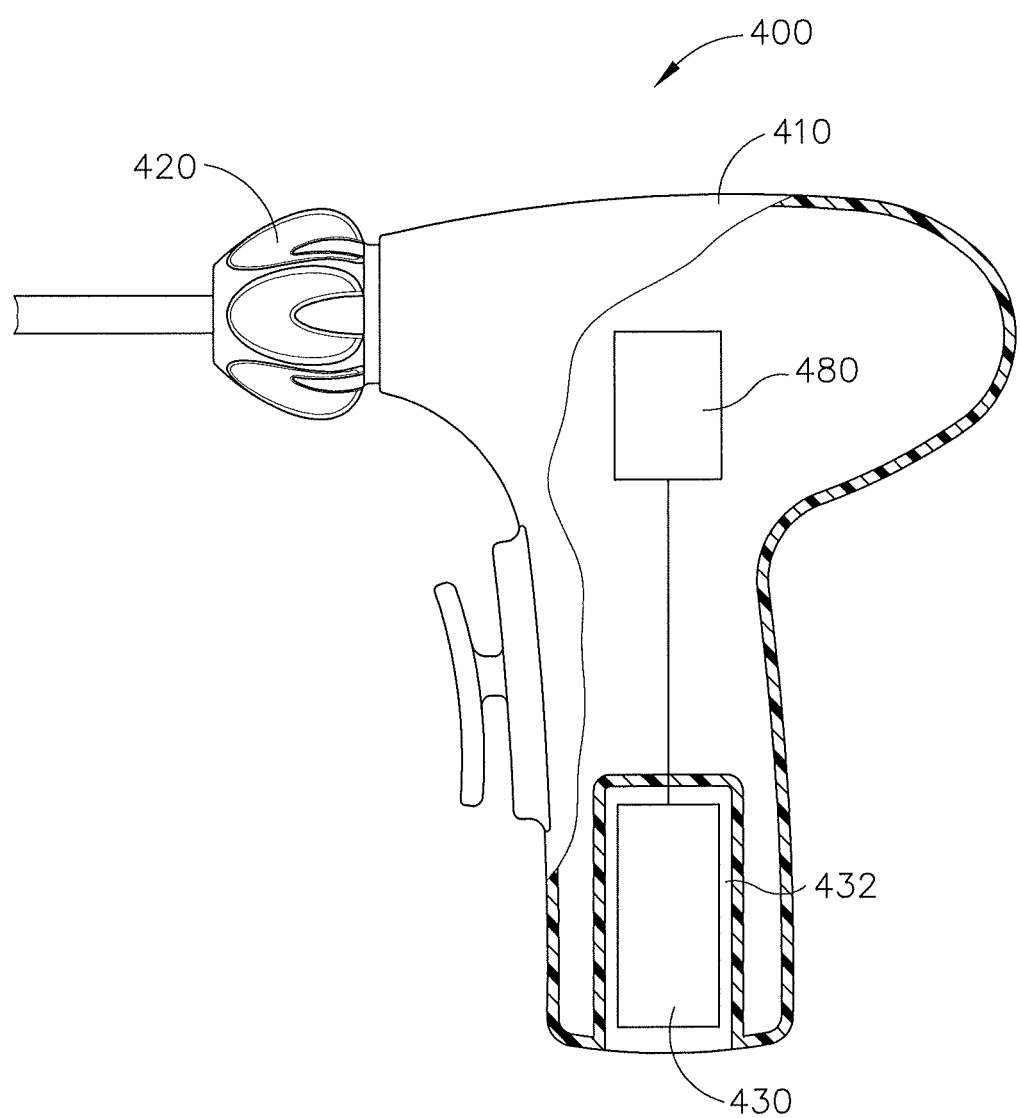
FIG. 4 depicts a side partially cross sectional view of an exemplary surgical instrument with a memory unit.

FIG. 4 depicts an exemplary surgical instrument (400) having a handle assembly (410) and a working end (420), which may comprise, for example, a transmission assembly with an end effector. Surgical instrument (400) further comprises a control unit (480) and a memory unit (430). It will be appreciated that surgical instrument (400) may be constructed according to or similar to the teachings regarding surgical instrument/medical device (10, 100).

Memory unit (430) may comprise a fixed memory or a removable memory in communication with control unit (480). Memory unit (430) may comprise a flash memory card that may be removable or fixed. In some versions where memory unit (430) is fixed in relation to handle assembly (410), it will be appreciated that handle assembly (410) may include a port for wired and/or wireless communication with memory unit (430). The present example comprises a removable memory plugged into a memory slot (432). Control unit (480) is operable to monitor the operation of surgical instrument (400) during use and write information regarding the use of surgical instrument (400) to memory unit (430). Such information may include technical specifications of surgical instrument (400) including, number of times operated, details of the last use, specifications during use of the various components making up surgical instrument (400). After usage and/or diagnostic information regarding surgical instrument (400) is written to memory unit (430), memory unit (430) information may be downloaded to be sent to the manufacturer. As a result, in the event that any errors occur during use of surgical instrument (400), the manufacturer or any other suitable party may be able to use information collected from memory unit (430) to diagnose any potential issues. In yet other exemplary versions, the entire memory unit (430) could be shipped to the manufacturer for diagnosis purposes. As a result, it will be appreciated that in either of these scenarios, the manufacturer or any other suitable support group may be able to diagnose surgical instrument (400) without the entire surgical instrument (400) being sent back to the manufacturer. It should be understood that surgical instrument (400) may be fully outfitted with sensors to facilitate operation of surgical instrument (400) being written to memory unit (430). As a result, memory unit (430) may serve as a "black box" for operations of surgical instrument (400), which may later be used for diagnosis and/or analyzing the operation of surgical instrument (400).

Memory unit (430) may also be loaded with user preference information such that when memory unit (430) is connected to surgical instrument (400), control unit (480) of surgical instrument (400) is operable to configure surgical instrument (400) according to the user preference data. Such user preference information may include maximum and minimum settings for surgical instrument (400) along with the particular procedure being performed by surgical instrument (400). Other suitable types of user preference information may be used as would be apparent to one of ordinary skill in the art in view of the teachings herein.

IV. Exemplary Remote Activation of Surgical Instrument

Figure 5:
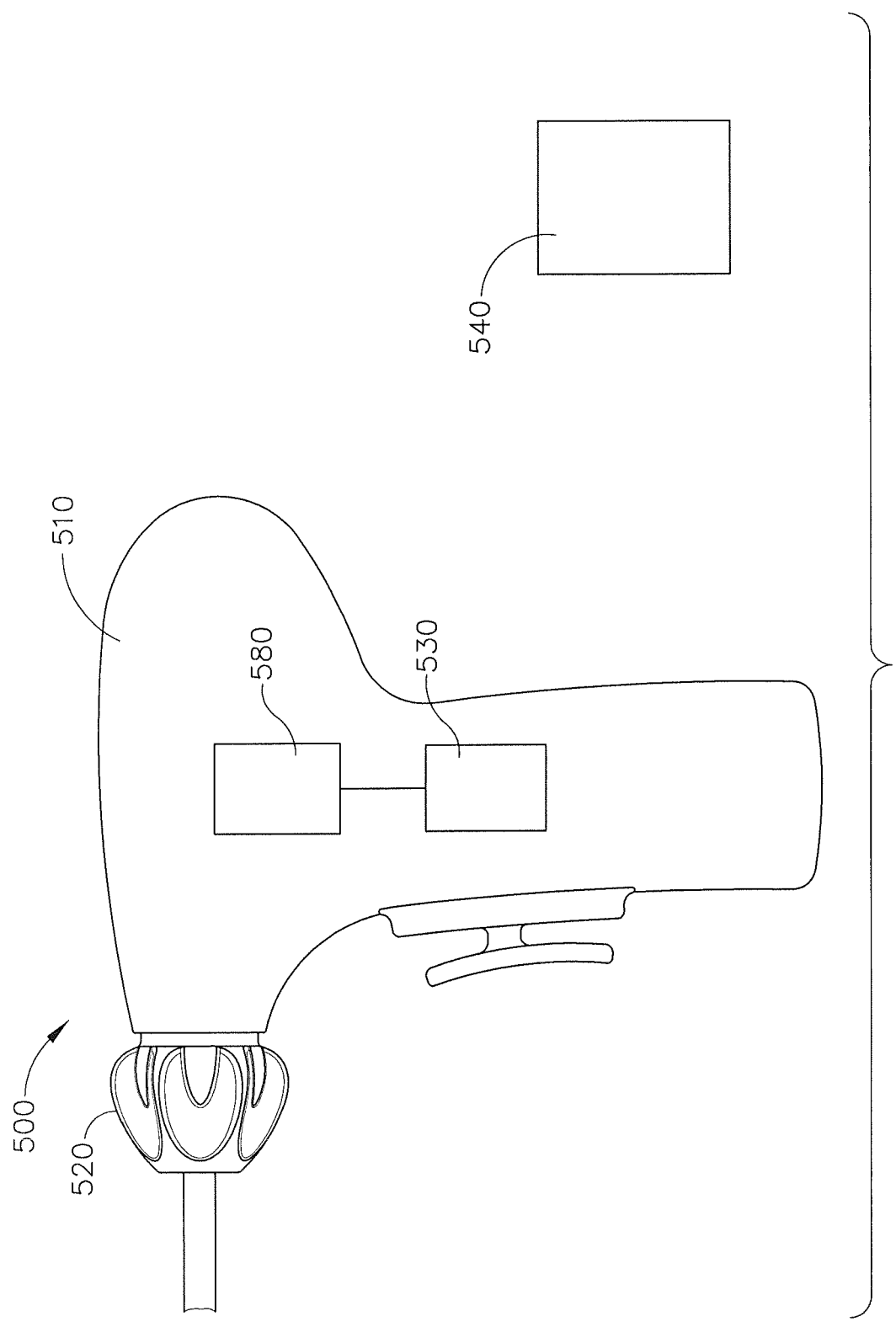
FIG. 5 depicts a side diagrammatic view of an exemplary surgical instrument with and external control.
Figure 6:
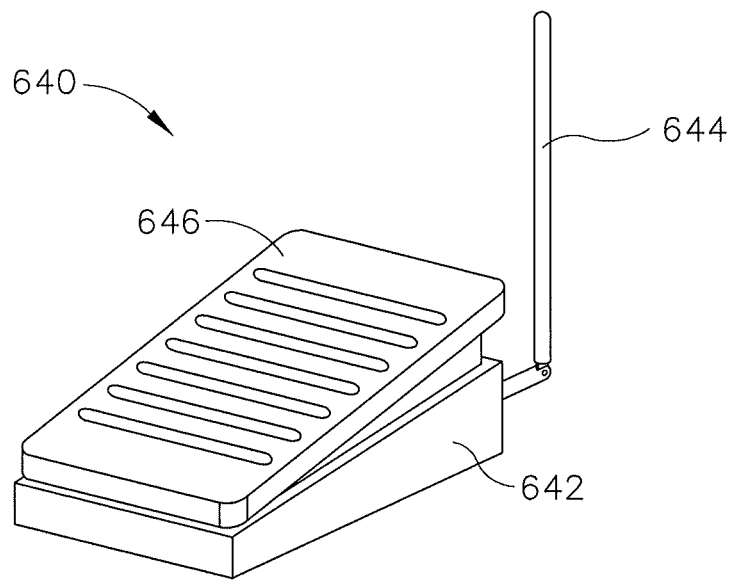
FIG. 6 depicts a side view of an exemplary foot pedal for use with the surgical instrument of FIG. 5.
Figure 7:
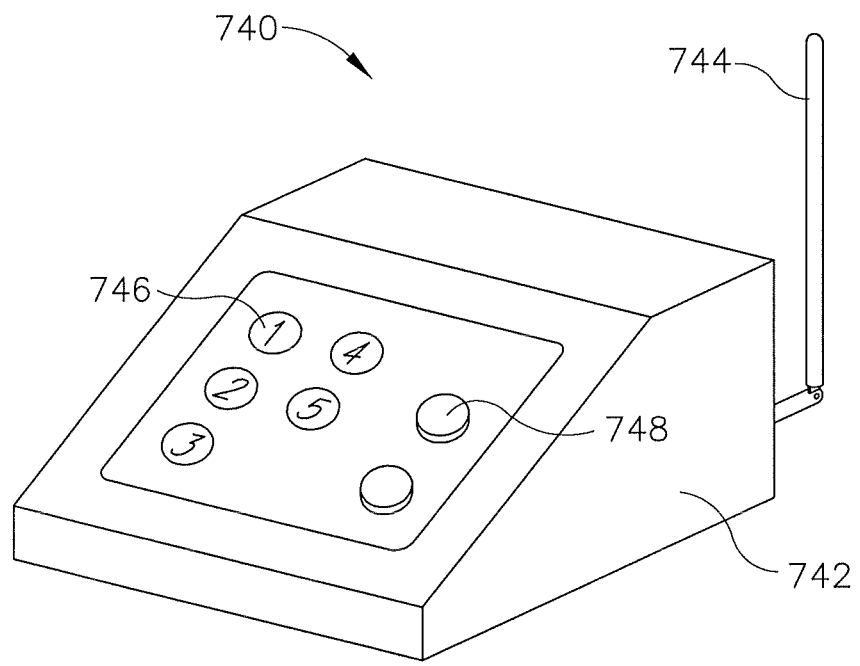
FIG. 7 depicts a perspective view of an exemplary external control for use with the surgical instrument of FIG. 5.

FIG. 5 depicts an exemplary surgical instrument (500) having a handle assembly (510) and a working end (520), which may comprise, for example, a transmission assembly with an end effector. Surgical instrument (500), which may be constructed similar to or in accordance with medical device and/or surgical instrument (10, 100), further comprises a control unit (580) and a communication device (530) in wireless communication with an external control (540). FIG. 6 shows one merely exemplary form that external control (540) may take. In particular, FIG. 6 shows an external control (640) comprising a footswitch having a body (642), an antenna (644), and a pedal (646). Antenna (644) is operable to transmit signals to communication device (530). Body (642) comprises a stable housing for external control (640), which may include a weighted bottom such that pedal (646) may be depressed without creating instability in the overall external control (640). Actuation of pedal (646) is operable to send an instruction signal from external control (640) to surgical instrument (500). For example, depressing pedal (646) may change the power level, speed, on/off state, or any other attribute of surgical instrument (500) as would be apparent to one of ordinary skill in the art in view of the teachings herein. FIG. 7 shows yet another exemplary form that external control (540) may take. In particular, FIG. 7 depicts external control (740) having a body (742) with user controls (748) and power level meter (746). As with the exemplary version shown in FIG. 6, external control (740) is operable to send instructions to surgical instrument (500) via antenna (744). Additionally, antenna (744) of FIG. 7 is operable to receive signals that may include information regarding power usage of surgical instrument (500). User controls (748) may comprise hardware buttons or soft keys on an LCD screen operable to determine the instructions to be transmitted to surgical instrument (500). For example, user controls (748) may be operable to set the power level of surgical instrument (500). In yet other versions, user controls (748) are operable to set the operating mode of surgical instrument (500), which may include selecting between a cutting mode and a coagulation mode. Power level meter (746) in the present example comprises a series of numerical indicators corresponding to a particular power level of surgical instrument (500) operable to inform the user of the current power level of surgical instrument (500). While the present example uses numerical indicators for power level meter (746), it will be appreciated that any suitable indicator may be used as would be apparent to one of ordinary skill in the art in view of the teachings herein. For example, power level meter (746) may comprise a bar meter, a circular meter, or any other suitable indicator.

V. Exemplary Battery Pack with Charger Unit

Figure 8:
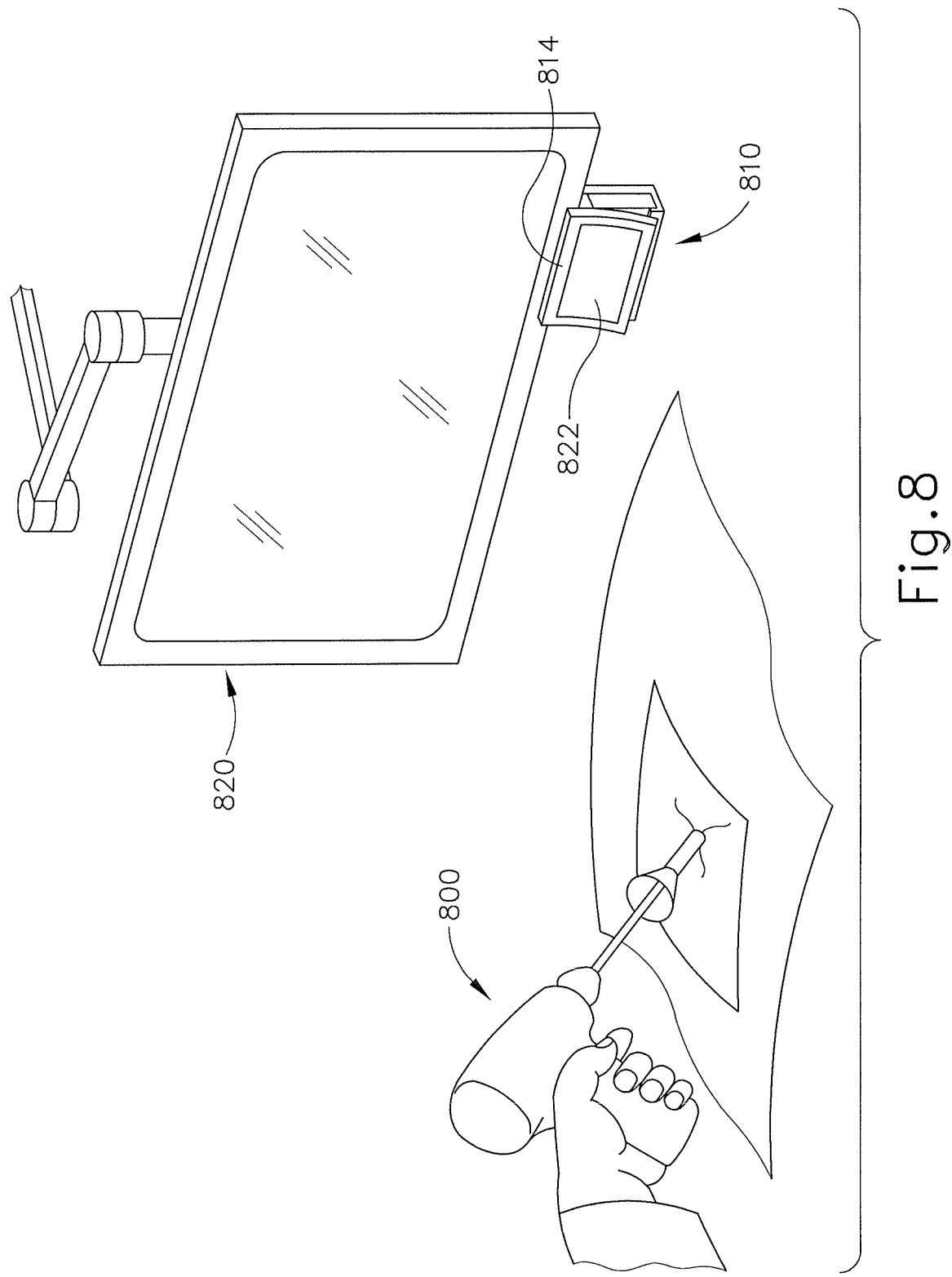
FIG. 8 depicts a perspective view of an exemplary surgical instrument with a monitor and an exemplary charger unit.
Figure 9:
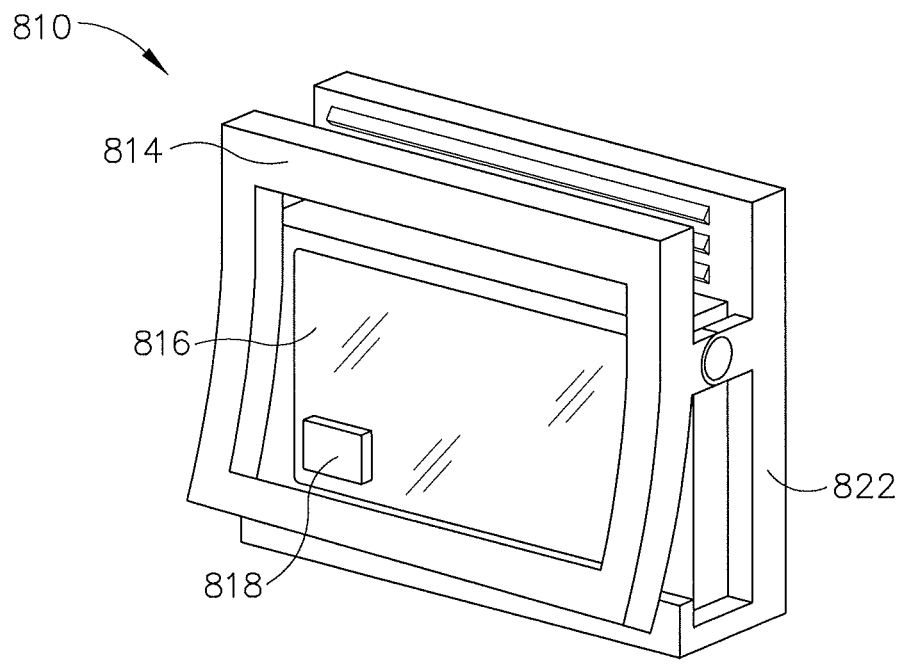
FIG. 9 depicts a front, perspective view of the exemplary charger unit of FIG. 8.
Figure 10:
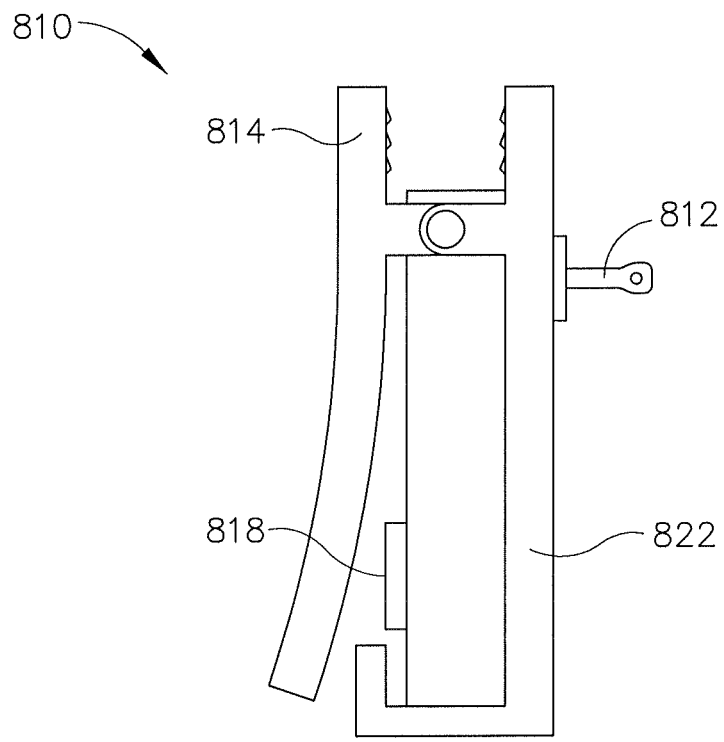
FIG. 10 depicts a side view of the exemplary charger unit of FIG. 8.

FIGS. 8-10 depict an exemplary charger unit (810) for use in conjunction with a surgical instrument (800) and a laparoscope monitor (820). In the present example, charger unit (810) comprises a body (822), a clamp portion (814), a plug (812), a display (816), and a communication module (818). Body (822), which can be seen in FIG. 9 from the front of body (822), has a rectangular shape, but it will be appreciated that any suitable shape for body (822) may be used as would be apparent to one of ordinary skill in the art in view of the teachings herein. Clamp portion (814), shown in FIG. 10 through a side view of body (822), comprises a pair of jaws biased toward each other such that clamp portion (814) is operable to grasp laparoscope monitor (820). Clamp portion (814) may be operable to grasp any suitable surface or member as would be apparent to one of ordinary skill in the art in view of the teachings herein. Plug (812) is operable to connect charger unit (810) to a wall outlet and draw power from the outlet to recharge rechargeable batteries contained within charger unit (810). In the present example, plug (812) is operable to fold into a recess formed within body (822). However, it will be appreciated that plug (812) may be fixed without being able to fold inward.

In some versions, charger unit (810) is operable to removably receive and recharge one or more batteries that are used to power surgical instrument (800). For instance, one rechargeable battery may be used in surgical instrument (800) while another rechargeable battery is charged/held in charger unit (810). Once the battery in surgical instrument (800) is depleted, it may be replaced with the fully charged battery from charger unit (810), and charger unit (810) may begin recharging the depleted battery. Since rechargeable batteries are stored within charger unit (810), it will be appreciated that the rechargeable batteries may be used to power the electrical functions of charger unit (810) as well. For instance, in settings where charger unit (810) is not coupled with plug (812) or plug (812) is not coupled with a wall outlet, charger unit (810) may run on one or more batteries in charger unit (810). Such batteries may be the same batteries used to power surgical instrument (800) or a dedicated backup battery. In versions where charger unit (810) has a dedicated backup battery, such a backup battery may also be used to recharge one or more batteries from surgical instrument (800). As another variation of charger unit (810) having a dedicated backup battery, charger unit (810) may simply run on the backup battery without also charging a battery from surgical instrument when charger unit (810) is not coupled with plug (812) or when plug (812) is not coupled with a wall outlet. Other suitable schemes will be apparent to those of ordinary skill in the art in view of the teachings herein.

Communication module (818) is operable to communicate wirelessly with surgical instrument (800). As a result, communication module (818) is operable to send and receive data from surgical instrument (800), which may include various diagnostic readings from surgical instrument (800). Charger unit (810) is then operable to output information from surgical instrument (800) to display (816). Display (816) may comprise an LCD screen operable to show diagnostic information and/or information regarding the operation of surgical instrument (800). Display (816) may output statuses regarding surgical instrument (800), alarms, troubleshooting help and advice, tissue feedback indicators, information related to the performance of surgical instrument (800), minimum and maximum values for battery and/or surgical instrument (800) power, power activation information of charger unit (810) or surgical instrument (800), tissue thickness information, cycle complete indicators, blade heat information, and/or any other suitable pieces of information as would be apparent to one of ordinary skill in the art in view of the teachings herein. For example, display (816) may be used to show the current power level of surgical instrument (800) or may be used to show a graphical representation of the internal operation of surgical instrument (800) such that the user may be able to use display (816) to monitor surgical instrument (800) during a surgical procedure. Laparoscope monitor (820) may be operable to view the surgical site as the surgical procedure is taking place. By attaching clamp portion (814) of charger unit (810) to laparoscope monitor (820), it will be appreciated that the user may simultaneously watch a real-time view of the surgical procedure while also monitoring diagnostic information regarding surgical instrument (800) on charger unit (810).

In some exemplary versions, it will be appreciated that charger unit (810) may further comprise a gravity sensor operable to detect the orientation of charger unit (810) such that charger unit (810) may be held in either a horizontal or a vertical orientation while maintaining a readable orientation for the user. In yet other exemplary versions, charger unit (810) may comprise a USB or other hardware ports operable to connect charger unit (810) to an external device to update the software of charger unit (810). In other exemplary versions, updated software may be transferred wirelessly to charger unit (810) to update the firmware or other software of charger unit (810).

VI. Exemplary Wireless Power Station

Figure 11:
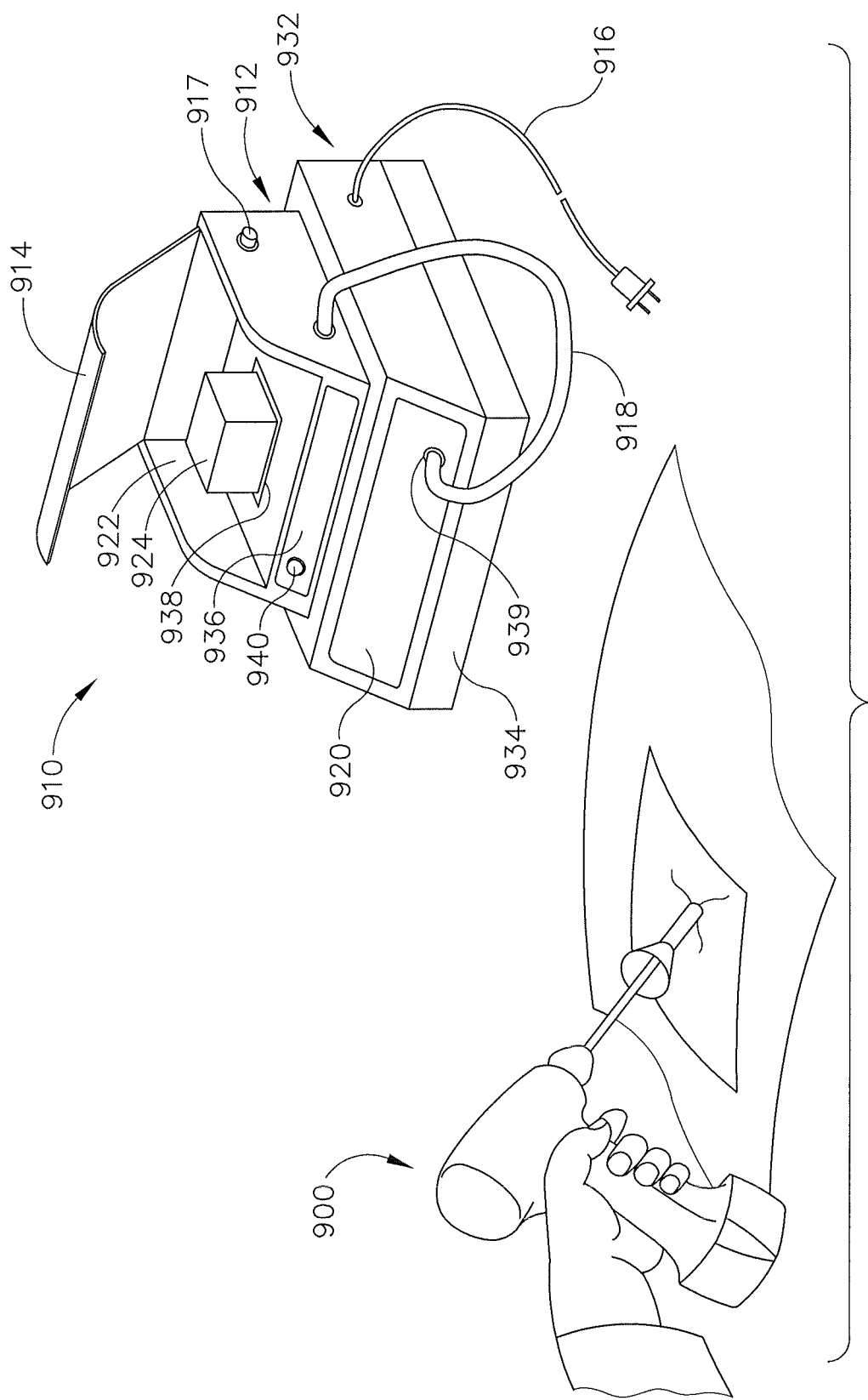
FIG. 11 depicts a perspective view of an exemplary surgical instrument with an exemplary charging station.
Figure 13:
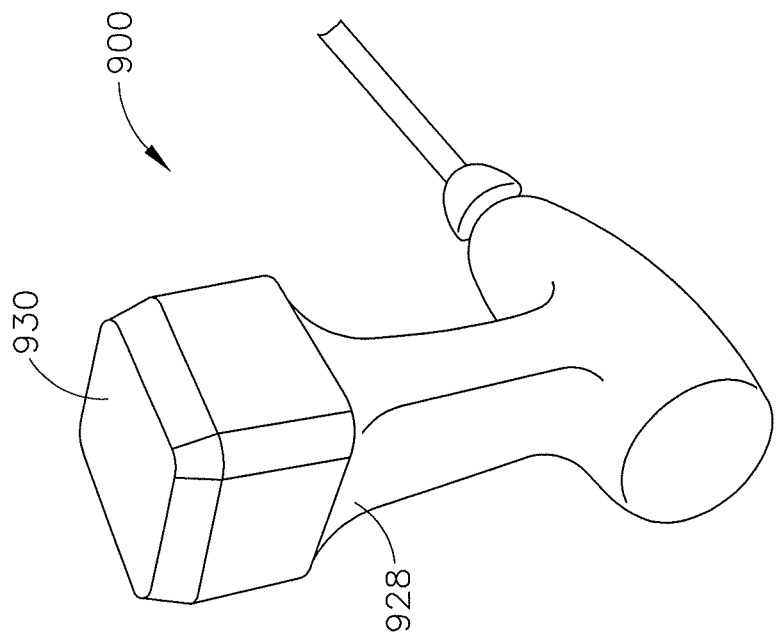
FIG. 13 depicts a rear, perspective view of the surgical instrument of FIG. 11 with the battery door closed.
Figure 12:
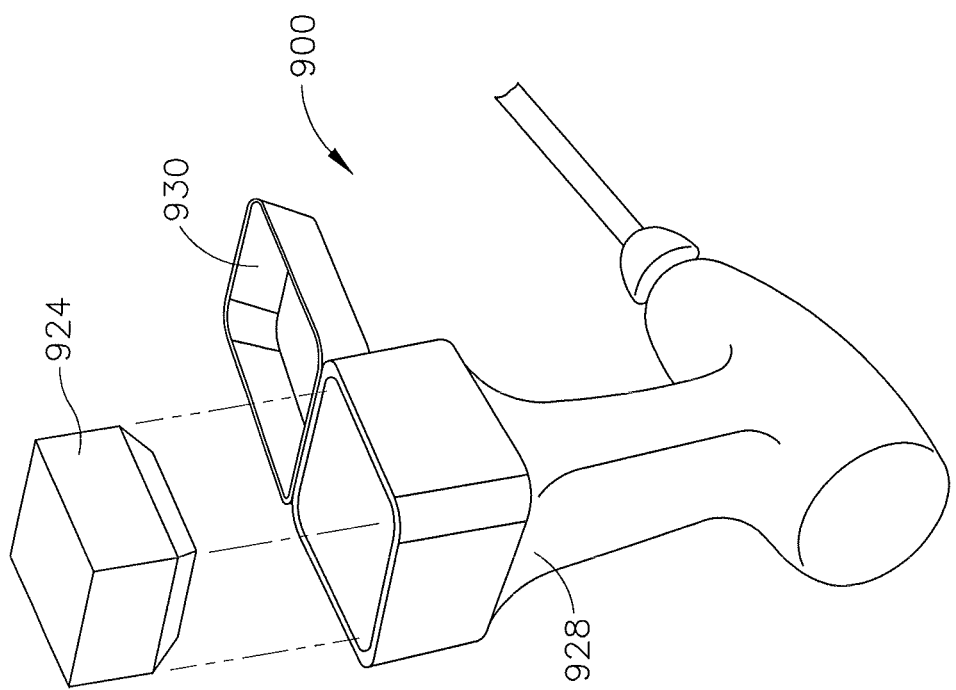
FIG. 12 depicts a rear, perspective view of the surgical instrument of FIG. 11 with a battery door opened.

FIGS. 11-13 show an exemplary surgical instrument (900) having a handle assembly (928) with a battery compartment (926) operable to hold a rechargeable battery (924). It will be appreciated that surgical instrument (900) may be constructed in accordance with the above teachings relating to medical device (10, 100) and/or the teachings of any of the references cited herein. FIG. 11 shows surgical instrument (900) being used in a surgical procedure and in communication with a charging station (910). Charging station (910) comprises a recharging container (912), a generator (932), and a platform (934). In the present example, recharging compartment (912) sits atop of generator (932), but any suitable configuration may be used. For example, recharging container (912) may be placed alongside generator (932), under generator (932), or may be incorporated into a single housing with generator (932). Other suitable configurations will be apparent to one of ordinary skill in the art in view of the teachings herein.

Recharging container (912) comprises a battery compartment (922) operable to hold a plurality of batteries (924). Recharging container (912) further comprises a lid (914) to selectively cover battery compartment (922). Battery compartment (922) comprises a rectangular receptacle operable to hold batteries (924), though it should be understood that any other suitable shape may be used. While recharging container (912) of the present example has just a single tier battery compartment (922), it should be understood that recharging container may include a plurality of tiers of battery compartments (922). The base of battery compartment (922) comprises a plurality of battery slots (938) where each slot (938) is operable to receive battery (924). Slots (938) may be constructed such that slots (938) provide a snapping sound or other form of feedback once battery (924) is sufficiently plugged into a slot (938). Slots (938) are spaced out such that batteries (924) may be individually grasped and removed from slots (938) without causing stress or undesirable forces being applied to adjacent batteries (924) from the user removing battery (924).

Slots (938) may be used with a light (940) such as an LED light operable to light up in different colors based on the charge status of batteries (924). In some exemplary versions, light (940) may be positioned adjacent to slot (938). For example, light (940) may light up red in the event that battery (924) attached to slot (938) is empty of charge. Slot (938) may light up yellow if battery (924) attached to slot (938) is currently charging, and slot (938) may light up green if battery (924) is fully charged. Other suitable configurations will be apparent to one of ordinary skill in the art in view of the teachings herein. For example, rather than different color lights (940), numerical indicators or any other suitable indicators may be used to indicate the relative charge states of battery (924) and/or other information relating to battery (924).

Lid (914) covering battery compartment (922) comprises a hinged lid attached to the rear of battery compartment (922). Furthermore, lid (922) is constructed of a translucent or transparent material such that the user may see into recharging container (912) as batteries (924) are being charged. By viewing batteries (924) through lid (922), the user can ascertain the charge states of batteries (924) without opening recharging container (912). While the present example comprises a hinged lid for lid (914), it will be appreciated that other configurations for lid (914) may be used such as a snap top lid, a sliding cover, etc., or any other suitable variation as would be apparent to one of ordinary skill in the art in view of the teachings herein.

The front of recharging container (912) comprises a display panel (936) operable to provide various information to the user including battery (924) charge levels. Other exemplary information may include displaying the total number of batteries (924) in battery compartment (922) as well as an on/off status of recharging container (912). Any other suitable information may be displayed on panel (936) as would be apparent to one of ordinary skill in the art in view of the teachings herein. Display panel (936) may be used in addition to or in lieu of lights (940).

Recharging container (912) is coupled with generator (932) via a communication cable (918), which is plugged into a universal port (939) of generator (932). Communication cable (918) is operable to deliver power as well as operation instructions from generator (932) to recharging container (912). Communication cable (918) may also transmit data from recharging container (912) to generator (932). In the present example, cable (918) is selectively retractable within recharging container (912). In particular, when retracted, cable (918) may be pulled to extend from recharging container (912). Recharging container (912) includes a retraction button (917) that may be pressed to retract extended cable (918) back into recharging container (912). A resilient member may bias cable (918) to a retracted position. Of course, retractability of cable (918) is merely optional.

Generator (932) is coupled with a power source (e.g., a wall outlet, etc.) via a power cord (916). Power cord (916) is thus operable to deliver power to generator (932) to thereby deliver power to recharging container (912) to recharge batteries (924). Generator (932) comprises a generator panel (920) operable to show the status of generator (932). Universal port (939) is shown as accepting a connection from recharging container (912) via cable (918), though it should be understood that universal port (939) is also operable to accept connections from ultrasonic surgical instruments and RF electrosurgical instruments. Generator (932) is thereby also operable to deliver power directly to ultrasonic surgical instruments and RF electrosurgical instruments. For instance, generator (932) may be compatible with any of the instruments taught in any of the references cited herein, among other types of instruments. Universal port (939) may comprise an RFID chip reader operable to read an RFID chip contained in a cable plug that is plugged into universal port (939). Thereafter, generator (932) can determine the identity of the device plugged into universal port (939) and determine the appropriate instructions and/or power parameters for properly operating the plugged in device. Other suitable ways of identifying a device plugged into generator (932) may be used as would be apparent to one of ordinary skill in the art in view of the teachings herein.

In some versions, recharging unit (912) may be connected to a network (e.g., the Internet, etc.) such that information stored on any memory units associated with recharging unit (912) transmitted over the network. Such information may include information regarding batteries (924), surgical instrument (900), the network, etc.; and may be sent to the user, a hospital, or the manufacturer, etc. Recharging unit (912) may also comprise a keyboard and/or other suitable input device such that the user may use to provide instructions to recharging unit (912) for charging batteries (924) and/or to command the transmission of information to and from recharging unit (912). It should be understood that generator (932) need not necessarily be included in such communications.

It will be appreciated that recharging container (912) is operable to transmit information to generator (932) including battery charge level information and identification information of generator (932) or any suitable information as would be apparent to one of ordinary skill in the art in view of the teachings herein. Generator panel (920) is operable to display information transferred from recharging container (912) and/or any other suitable information as would be apparent to one of ordinary skill in the art in view of the teachings herein. In the event that an ultrasonic instrument or an RF based instrument is connected directly to generator (932), the ultrasonic and/or RF based instrument may be able to transmit information regarding the operation and/or status of the ultrasonic and/or RF based instrument, which may be output entirely or in part to generator panel (920). By way of example only, generator (932) and associated components may be configured in accordance with the teachings of U.S. Patent App. Publ. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. While the present example shows generator (932), it will be appreciated that in some versions, generator (932) may be removed such that recharging station (912) is simply plugged directly into a wall.

Furthermore, it is contemplated that recharging container (912) may be in wireless communication with surgical instrument (900) such that surgical instrument (900) is operable to transfer information to recharging container (912) regarding diagnostic and/or status information of surgical instrument (900) or any other information as would be suitable to one of ordinary skill in the art in view of the teachings herein. For instance, surgical instrument (900) may transmit information to recharging container (912) regarding the charge status of a battery (924) contained within surgical instrument (900). Recharging container (912) may provide an audio and/or visual alert to the user when the charge level of the battery (924) in surgical instrument (900) falls below a threshold, thereby alerting the user to replace battery (924). It will be appreciated that any information sent from surgical instrument (900) may also be output to generator (932) to display on generator panel (912) and/or for other processing by generator (932). It will be appreciated that generator (932) may be used to show information regarding surgical instrument (900) as if generator (932) were directly connected to surgical instrument (900).

When battery (924) is ready for use, FIG. 12 shows battery (924) being dropped into handle assembly (928) of surgical instrument (900) by opening battery door (930) and dropping in battery (924). In some exemplary versions, battery (924) may have an asymmetrical shape with handle assembly (928) having a complementary shape such that battery (924) can only be dropped into handle assembly (928) in one orientation. Battery (924) may be handled appropriately by, for example, a technician or surgeon with sterile hands, such that replacing battery (924) does not compromise the sterility of handle assembly (928). FIG. 13 shows battery door (930) being shut and surgical instrument (900) being ready for use.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using a surgical system, the surgical system comprising a powered surgical instrument, a control unit located within the powered surgical instrument, a communication device located within the surgical instrument, and an external device, wherein the control unit and the communication device are in communication with each other, wherein the external device is configured to communicate information with the control unit via the communication device, the method comprising:
    (a) presenting a plurality of surgical procedures on the external device, wherein each surgical procedure in the plurality of surgical procedure comprises a specific set of instructions with distinct operational parameters for the control unit;
    (b) receiving a selection of a surgical procedure from the plurality of surgical procedures;
    (c) generating and transmitting the specific set of instructions corresponding to the selected surgical procedure from the external device to the communication device;
    (d) using the instructions corresponding to the selected surgical procedure transmitted from the external device to the communication device to establish operational parameters of the surgical instrument with the control unit; and
    (e) limiting the powered surgical instrument within the established operational parameters while the powered surgical instrument is activated.

2. The method of claim 1, wherein the powered surgical instrument further comprises a sensor in communication with the control unit, wherein the sensor is adapted to collect information, the method further comprising:
    (a) collecting sensor information at the control unit, wherein the sensor information is from the powered surgical instrument,
    (b) sending the sensor information from the control unit to the communication device; and
    (c) sending the sensor information from the communication device to the external device.

3. The method of claim 2, further comprising displaying the sensor information on the external device.

4. The method of claim 2, further comprising:
    (a) detecting an error with the control unit during operation of the powered surgical instrument based on a measurement from the sensor;
    (b) generating an error code with the control unit;
    (c) communicating the error code to the communication device with the control unit; and
    (d) communicating the error code to the external device with the communication device.

5. The method of claim 4, further comprising displaying the error code on the external device.

6. The method of claim 4, further comprising transmitting the error code to an outside location through the external device.

7. The method of claim 1, wherein the specific set of instructions further comprises a distinct set of diagnostic instructions.

8. The method of claim 7, wherein the powered surgical instrument further comprises a plurality of sensors, wherein the distinct set of diagnostic instructions comprises instructions to record readings at particular sensors within the plurality of sensors.

9. The method of claim 1, further comprising sending diagnostic information from the control unit to the external device via the communication device.

10. The method of claim 9, further comprising displaying the diagnostic information on the external device.

11. The method of claim 1, further comprising:
    (a) sending updated software from the external device to the communication device;
    (b) sending updated software from the communication device to the control unit; and
    (c) utilizing the updated software by the control unit to operate the powered surgical instrument.

12. The method of claim 11, further comprising:
(a) communicating with a remote site via the internet, wherein the act of communicating with a remote site via the internet is performed by the external device; and
(b) checking for the most updated software with the remote site before sending the updated software to the communication device, wherein the act of checking for the most updated software is performed by the external device.

13. The method of claim 12, further comprising automatically sending the updated software to the communication device if the external device detects a more updated software, wherein the act of automatically sending the updated software is performed by the external device.

14. The method of claim 12, further comprising displaying a message to confirm user intent to receive updated software before sending updated software to the communication device, wherein the act of displaying a message is performed by the external device.

15. The method of claim 11, wherein the updated software comprises a set of instructions limiting a number of uses for the powered surgical instrument.

16. The method of claim 1, further comprising:
(a) sending automated diagnostic commands to the communication device, wherein the act of sending automated diagnostic commands to the communication device is performed by the external device, and
(b) sending automated diagnostic commands to the control unit, wherein the act of sending automated diagnostic commands to the control unit is performed by the communication device.

* * * * *